United States Patent
Mahoney

(10) Patent No.: US 9,370,459 B2
(45) Date of Patent: *Jun. 21, 2016

(54) SYSTEM AND METHOD FOR ALERTING VISUALLY IMPAIRED USERS OF NEARBY OBJECTS

(75) Inventor: Andrew Mahoney, Toronto (CA)

(73) Assignee: Andrew Mahoney, Toronto, ON (CA)

( * ) Notice: Subject to any disclaimer, the term of this patent is extended or adjusted under 35 U.S.C. 154(b) by 454 days.

This patent is subject to a terminal disclaimer.

(21) Appl. No.: 13/310,158

(22) Filed: Dec. 2, 2011

(65) Prior Publication Data

US 2012/0092460 A1    Apr. 19, 2012

Related U.S. Application Data

(63) Continuation-in-part of application No. 13/375,316, filed as application No. PCT/CA2010/000904 on Jun. 18, 2010.

(60) Provisional application No. 61/218,745, filed on Jun. 19, 2009.

(51) Int. Cl.
*A61H 3/06* (2006.01)
*G09B 21/00* (2006.01)
*G06K 9/00* (2006.01)
*A61F 9/08* (2006.01)

(52) U.S. Cl.
CPC ............ *A61H 3/061* (2013.01); *G06K 9/00664* (2013.01); *G09B 21/007* (2013.01); *A61F 9/08* (2013.01); *A61H 2201/5092* (2013.01)

(58) Field of Classification Search
CPC ............ A61H 3/061; A61H 2003/065; A61H 2003/063; G01C 21/00
See application file for complete search history.

(56) References Cited

U.S. PATENT DOCUMENTS

| 6,320,496 | B1 | 11/2001 | Sokoler et al. |
| 7,630,806 | B2 | 12/2009 | Breed |
| 2004/0246135 | A1 | 12/2004 | Carey |
| 2006/0024647 | A1 | 2/2006 | Chesnais et al. |

(Continued)

FOREIGN PATENT DOCUMENTS

| EP | 1035463 | 9/2000 |
| EP | 1970877 | 9/2008 |
| JP | 2002065721 | 3/2002 |

OTHER PUBLICATIONS

Zhu et al. (Fusion of Time-of-Flight Depth and Stereo for High Accuracy Depth Maps, Computer Vision and Pattern Recognition, 2008).*

(Continued)

*Primary Examiner* — Mohammed Jebari
(74) *Attorney, Agent, or Firm* — McMillan LLP

(57) ABSTRACT

A system and method for assisting a visually impaired user including a time of flight camera, a processing unit for receiving images from the time of flight camera and converting the images into signals for use by one or more controllers, and one or more vibro-tactile devices, wherein the one or more controllers activates one or more of the vibro-tactile devices in response to the signals received from the processing unit. The system preferably includes a lanyard means on which the one or more vibro-tactile devices are mounted. The vibro-tactile devices are activated depending on a determined position in front of the user of an object and the distance from the user to the object.

7 Claims, 14 Drawing Sheets

(56) References Cited

U.S. PATENT DOCUMENTS

| | | |
|---|---|---|
| 2007/0016425 A1 | 1/2007 | Ward |
| 2008/0120029 A1 | 5/2008 | Zelek et al. |
| 2008/0170118 A1* | 7/2008 | Albertson et al. ............... 348/46 |
| 2008/0226134 A1 | 9/2008 | Stetten et al. |

OTHER PUBLICATIONS

Shawki, Arebi and John Zelek , "A Smart Reconfigurable Visual System for the Blind".

M. Bouzit, A Chaibi, K.J. De Laurentis, and C. Mavroidis, "Tactile Feedback Navigation Handle for the Visually Impaired", 2004, Anaheim, California USA.

Simeon, Keates, Accessibility and Computing, 2006.

Wai Yu, Kenneth Guffie and Stephen Brewster, Image to Haptic Data Conversion: A First Step to Improving Blind People's Accessibility to Printed Graphs.

Stephen Brewster, John Zelek, Richard Audette, Jocelyn Balthazaar, Graig Dunk, A Stereo-vision System for the Visually Impaired.

John Zelek, "Seeing by touch (haptics) for wayfinding", 2005, Waterloo, Ontario.

* cited by examiner

SYSTEM AND METHOD FOR ALERTING VISUALLY IMPAIRED USERS OF NEARBY OBJECTS

CROSS REFERENCE TO RELATED APPLICATIONS

This application is a Continuation-In-Part of U.S. application Ser. No. 13/375,316 filed Nov. 30, 2011, which was a 371 National Phase of PCT/CA2010/000904 filed Jun. 18, 2010, which claimed priority to U.S. Provisional Application No. 61/218,745 filed Jun. 19, 2009.

FIELD OF THE INVENTION

The present invention relates to the field of object detection method and systems for the visually impaired, and in particular, it relates to a system and method for alerting visually impaired users of nearby objects, especially those beyond the reach of a cane.

BACKGROUND OF THE INVENTION

Many people living with complete blindness do not leave their homes without a sighted person. Even those with the skill and courage to use the long cane avoid areas with many street obstacles such as poles, planters, and benches. As a result these people can be isolated and have strict limitations on when and where they can travel in their daily lives. Generally, when moving around, the awareness of surrounding objects is provided by the users hearing and the sensing of objects using a cane. There is a need in the art for a device to alert users of surrounding objects, beyond the reach of a cane.

SUMMARY OF THE INVENTION

According to one embodiment of the invention, there is provided a system for assisting a visually impaired user comprising (a) an imaging device; (b) a processing unit for receiving images from the imaging device and converting the images into signals for use by one or more controllers; and, (c) one or more vibro-tactile devices; wherein the one or more controllers activates one or more of the vibro-tactile devices in response to the signals received from the processing unit.

According to one aspect of the invention, the system includes a lanyard means sized and otherwise dimensioned to be worn around a neck of the user, wherein the one or more vibro-tactile devices are mounted on the lanyard means. Preferably, the one or more vibro-tactile devices comprises first, second, and third vibro-tactile devices; the first vibro-tactile device positioned on a right side of the lanyard means, the second vibro-tactile device positioned on a left side of the lanyard means, and the third vibro-tactile device positioned on a top end of the lanyard means, thereby providing for a vibro-tactile device positioned at a right side of the user, a left side of the user, and at a center position proximate the neck of the user when the lanyard means is worn.

According to another aspect of the invention, the imaging device and the processing unit are mounted at a bottom end of the lanyard means such that the imaging device and the processing unit are positioned proximate a chest portion of the user when the lanyard means is worn.

Preferably, the imaging device includes left and right imagers; said left and right imagers positioned and arranged to provide stereoscopic images to said processing unit, and the processing unit includes an image processing unit. The image processing unit is adapted to create rectified images to eliminate distortion in the images provided by the imagers and to create a depth map from the stereoscopic images.

In one embodiment of the invention, the imaging device includes a time of flight camera; said time of flight camera is positioned and arranged to provide depth images, or depth maps, to said processing unit, and the processing unit includes an image processing unit.

According to another aspect of the invention, the processing unit creates a three-dimensional reconstruction based on data from the depth map, the three-dimensional space in front of the user is divided into a plurality of volumes of space, and the processing unit determines whether objects in front of the user reside in one or more of the plurality of volumes of space. The processing unit further produces a signal representative of the one or more volumes of space occupied by the objects. The signal is preferably representative of a direction and distance from the user of the objects. Preferably, the signal is transmitted to the one or more controllers which activate one or more of the first, second and third vibro-tactile devices in response to the signal. The first vibro-tactile device being activated when the signal indicates the presence of the object generally to the right of the user, the second vibro-tactile device being activated when the signal indicates the presence of the object generally to the left of the user, and the third vibro-tactile device being activated when the signal indicates the presence of said object generally in front of the user. According to another aspect, the controller activates the vibro-tactile devices with an intensity proportionate to the distance from said user of the object.

According to another embodiment of the invention, the system further includes audio alert means arranged such that the controller activates the audio alert means when the signal indicates the presence of the object at face level of the user.

According to another embodiment the images to generate a signal for use by one or more controllers, activating one or more vibro-tactile devices in response to the signal received from the one or more controllers.

According to one aspect of the second embodiment, there is provided lanyard means sized and otherwise dimensioned to be worn around a neck of the user, wherein the one or more vibro-tactile devices are mounted on the lanyard means. Preferably, the one or more vibro-tactile devices comprises first, second, and third vibro-tactile devices; the first vibro-tactile device positioned on a right side of the lanyard means, the second vibro-tactile device positioned on a left side of the lanyard means, and the third vibro-tactile device positioned on a top end of the lanyard means, thereby providing for a vibro-tactile device positioned at a right side of the user, a left side of the user, and at a center position proximate the neck of the user when the lanyard means is worn.

According to another aspect of the second embodiment, the imaging device comprises left and right imagers positioned and arranged to provide stereoscopic images to said processing unit. The processing unit includes an image processing unit and the method further includes creating rectified images to eliminate distortion in the images provided by the imagers and creating a depth map from the stereoscopic images.

According to another aspect of the second embodiment, the imaging device comprises a time of flight camera positioned and arranged to provide a depth image or depth map to said processing unit. The processing unit includes an image processing unit and the method further includes creating rectified images to eliminate distortion in the images provided by the imagers.

According to another aspect of the second embodiment, the method further includes creating a three-dimensional reconstruction based on data from the depth map, dividing the three-dimensional space in front of the user into a plurality of volumes of space, determining whether objects in front of the user reside in one or more of the plurality of volumes of space, and producing a signal representative of the one or more volumes of space occupied by the objects, wherein the signal is representative of a direction and distance from the user of the objects.

According to another aspect of this embodiment, the signal is transmitted to the one or more controllers which activate one or more of the first, second and third vibro-tactile devices in response to the signal. The first vibro-tactile device being activated when the signal indicates the presence of the object generally to the right of the user, thed second vibro-tactile device being activated when the signal indicates the presence of the object generally to the left of the user, and the third vibro-tactile device being activated when said signal indicates the presence of the object generally in front of the user. The vibro-tactile devices may also be activated with an intensity proportionate to the distance from the user of the objects. The method may further include generating an audio alert when the signal indicates the presence of the object at face level of the user.

It is an object of this invention to partially or completely fulfill one or more of the above-mentioned needs.

BRIEF DESCRIPTION OF THE DRAWINGS

The invention will now be described in more detail, by way of example only, with reference to the accompanying drawings, in which like numbers refer to like elements, wherein.

DETAILED DESCRIPTION OF THE PREFERRED EMBODIMENTS

Figure 1:
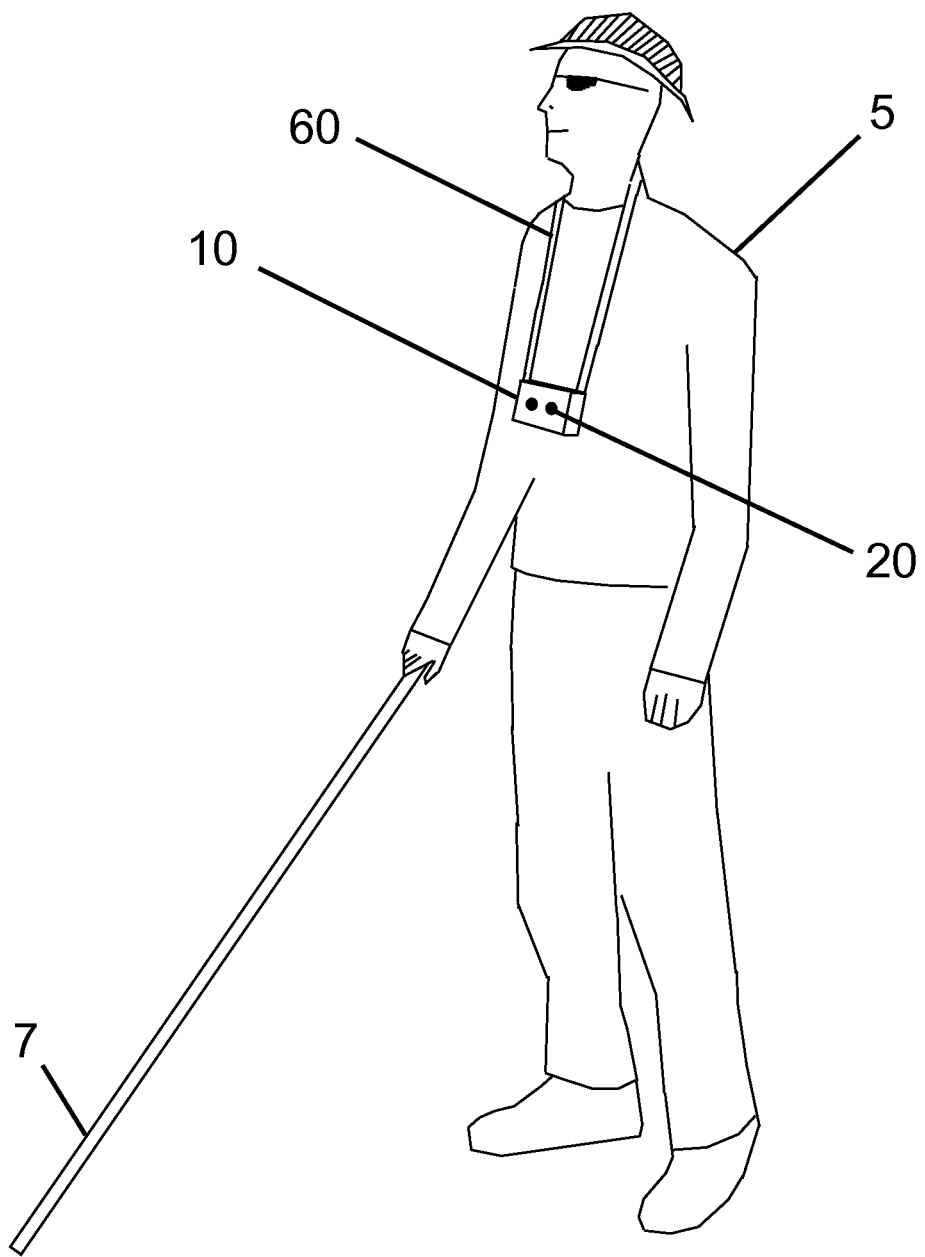
FIG. 1 shows the system of the invention worn on a user.
Figure 2:
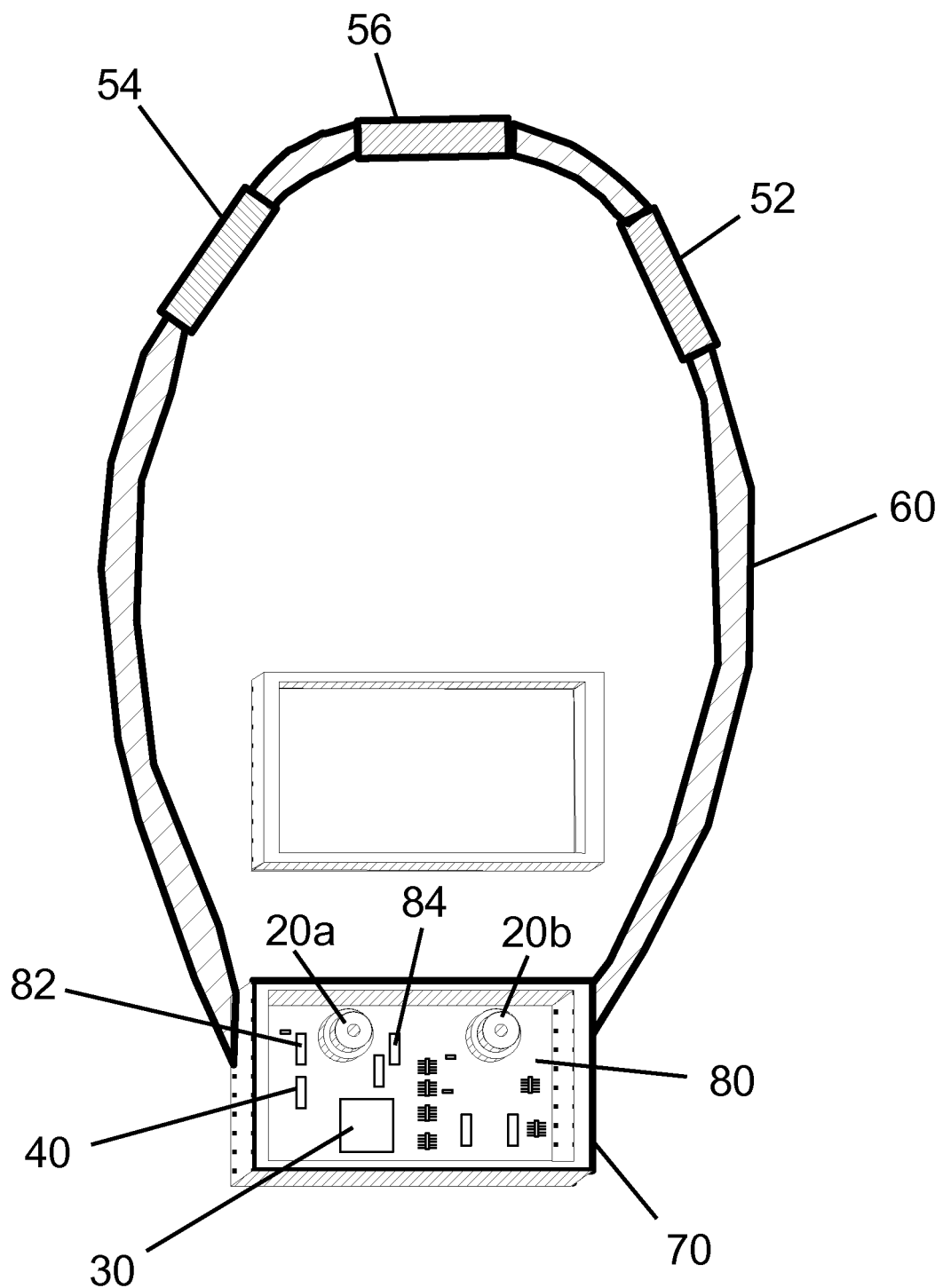
FIG. 2 is a top schematic view of the system according to the invention.
Figure 3:
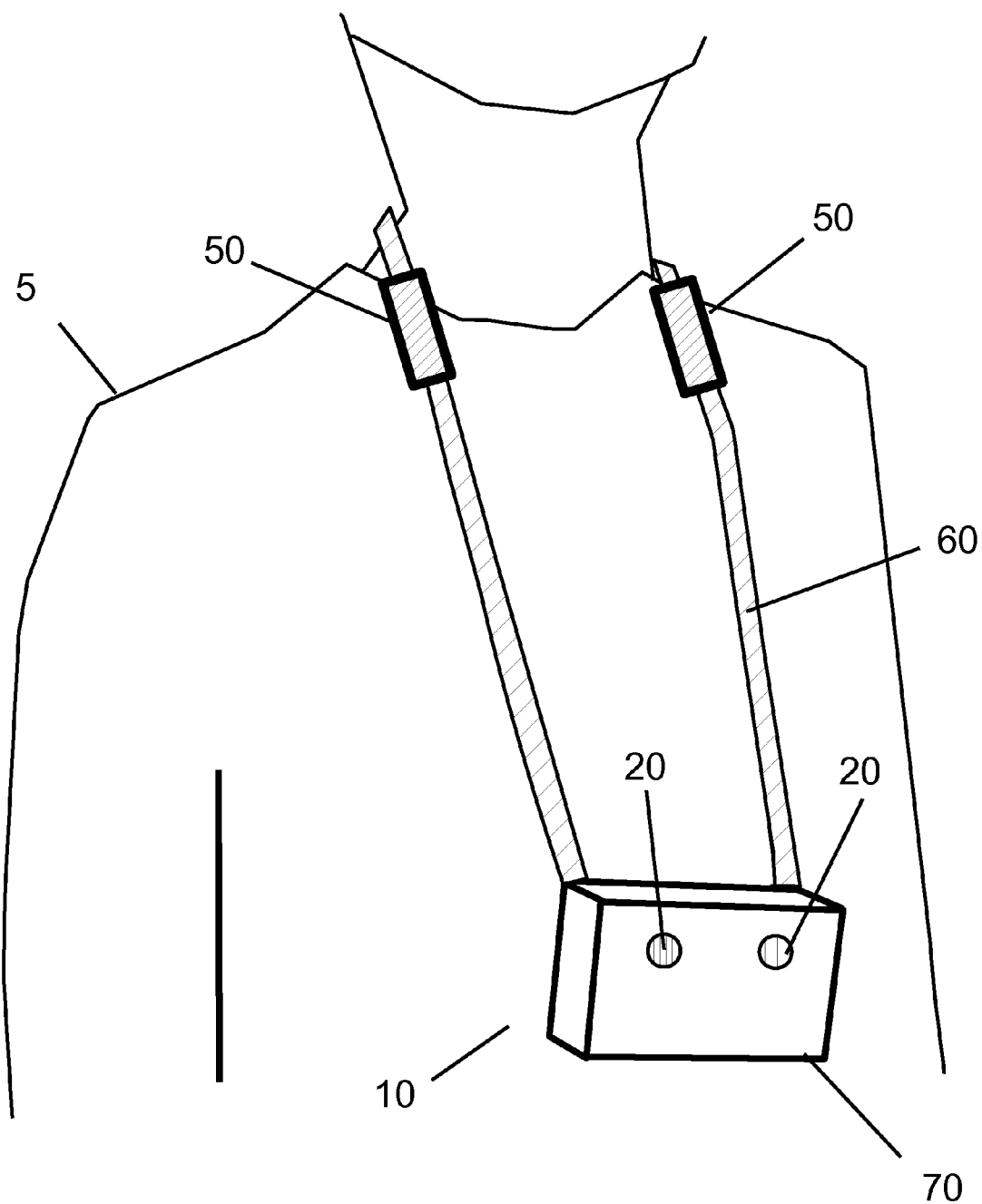
FIG. 3 is a close up view of the system worn by the user as shown in FIG. 1.
Figure 4:
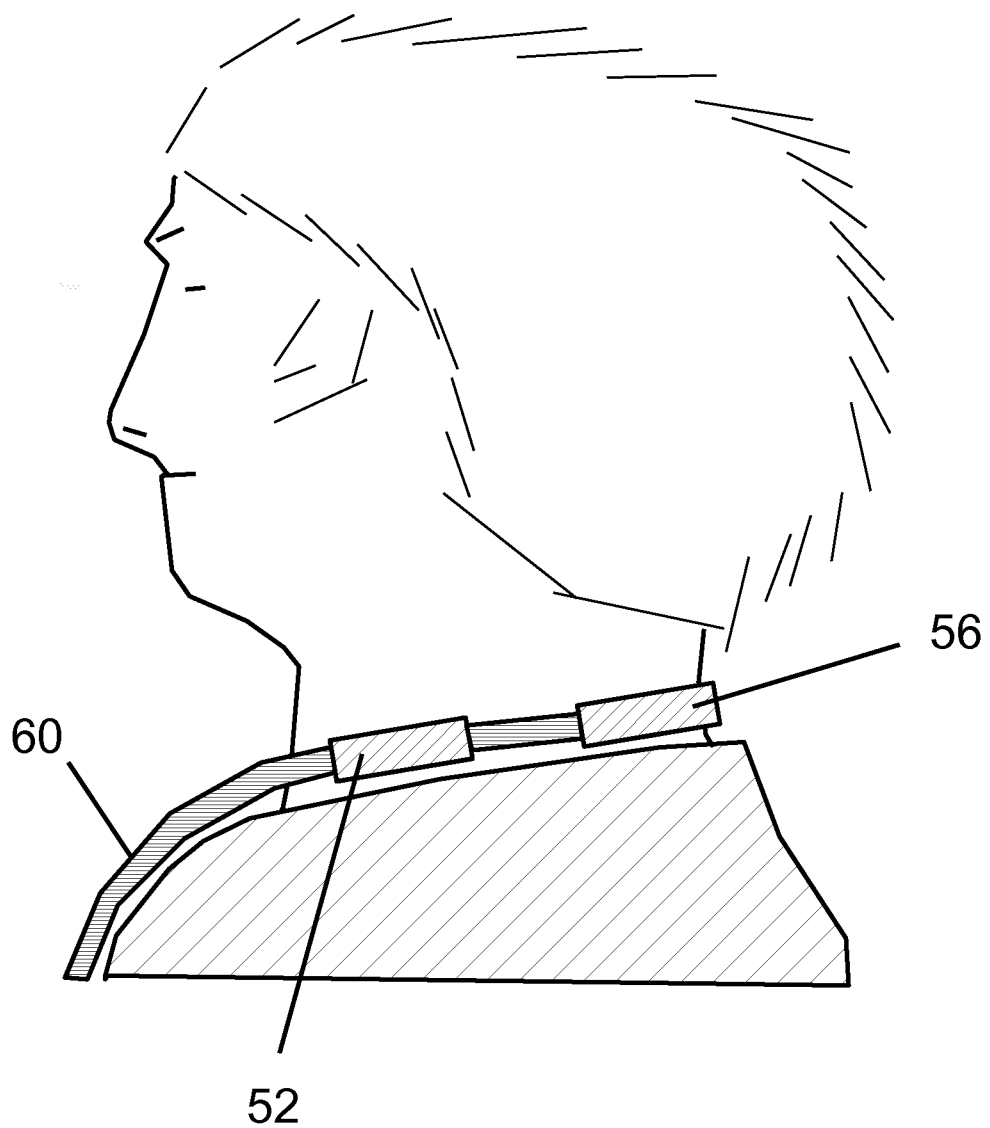
FIG. 4 is a back view of the system worn by the user.

Referring to FIGS. 1 to 4, the invention generally includes a system 10 for assisting a visually impaired user 5 including an imaging device 20, a processing unit 30 for receiving images from the imaging device and converting the images into signals for use by a controller 40, and one or more vibro-tactile devices 50 activated by the controller 40 in response to signals received from the processing unit 30. The invention assists a blind cane user 5 by alerting of dangers and obstacles beyond the reach of their cane 7. The invention alerts the user of obstacles by activating vibrating vibro-tactile devices 50 that rest on, or adjacent to, the skin of the user's neck. Preferably, the location of each vibro-tactile device 50, and the strength of vibration from each vibro-tactile device 50 indicates the direction and distance to obstacles, as will be explained in further detail below. The system 10 is preferably portable and battery powered. As will be appreciated by a person skilled in the art, the system 10 does not obstruct any remaining vision that a visually disabled user may have.

According to the preferred embodiment, the system 10 includes lanyard means 60 sized and otherwise dimensioned to be worn around a neck of the user, in a manner similar to a necklace. The lanyard means may be formed from a natural rubber tubing, of the type generally referred to as surgical tubing. Electrical wiring means to connect the controller 40 to the vibro-tactile devices 50 may be routed within the tubing.

The vibro-tactile devices 50 are mounted on the lanyard means. As shown in the illustrated embodiment, there system 10 includes first, second, and third vibro-tactile devices 52, 54, 56. The first vibro-tactile device 52 may be positioned on a right side of the lanyard means 60, the second vibro-tactile device 54 on the left side of the lanyard means 60, and the third vibro-tactile device 56 on a top end of the lanyard means 60. In this manner, a vibro-tactile device 52, 54, 56 is positioned at a right side of the user 5, the left side of the user 5 and at a centre position of the user 5, proximate the back of the user's neck when the lanyard means 60 is worn. According to the preferred embodiment, the third vibro-tactile device 56 is positioned at a mid-point of the lanyard means 60, the second vibro-tactile device 54 and the first vibro-tactile device 52 are positioned at equidistant points from the third vibro-tactile device 56, in opposite directions thereof, and preferably, when worn by the user around the neck, the first and second vibro-tactile devices 52, 54, are arranged at an angle of approximately 45 degrees from the third vibro-tactile device 56, in opposite directions thereof.

The imaging device 20 and the processing unit 30 are mounted at a bottom end of the lanyard means 60 such that the imaging device 20 and the processing unit 30 are positioned proximate a chest portion of the user 5 when the lanyard means 60 is worn. In this manner, the system 10 appears as a type of neck-worn camera device and is relatively inconspicuous. Furthermore, the system 10 is easily donned and doffed without assistance from other people or without complex mounting requirements.

The vibro-tactile devices 50 are preferably manufactured by installing a motor into a housing adapted to be mounted onto the lanyard means 60. The motor, may, for example be one produced and sold by Jameco under part number 7ZK681. Various other forms of vibro-tactile devices 50 may also be used. The controller is adapted to activate the motor and generate vibrations indicative of a distance and direction of an object from the user. Other means and mechanisms for the generation of vibration in response to a signal are known and otherwise not further herein described. Vibrations produced by the vibro-tactile devices 50 are generated in response to a signal received by the controller 40. The signal from the controller 40 includes information as to the direction and distance from the user to an object.

Preferably, the location of the vibration, as dictated by one of the vibro-tactile device directs the user's attention to that direction. The left vibro-tactile device 54 indicates an object in front of the person to the left. The center vibro-tactile device 56 indicates an object to the front or center direction. Likewise the right vibro-tactile device 52 indicates an object to the right. The intensity of vibration of a vibro-tactile device is indicative of the distance from the object to the user. Preferably, strong vibration intensity indicates close proximity. Medium vibration intensity indicates middle distance objects. Weak vibration intensity indicates distant objects. A lack of vibration indicates no objects. Alternatively, rather than varying the vibration intensity to indicate a distance to the object, a length of vibration may be used. Thus, longer periods of vibration may be used to indicate closer objects and shorter periods of vibration may be indicative of more distant objects. Preferably, the correlation between distance and intensity of vibration (or length of vibration) will be customizable, such that a user, either on their own or with the help of a technician, can alter these settings to accommodate for a particular user's sensitivity.

The imaging device 20 preferably comprises two camera lenses 20a and 20b, positioned laterally spaced from each other and arranged to take stereoscopic images. The lenses 20a and 20b are preferably mounted within a housing 70 that holds the processing unit 30, controller 40, and all related hardware and power elements, such as a battery, preferably a lithium ion battery, and related hardware required to transmit signals to the vibro-tactile devices. The housing 70 preferably includes a cover to enclose the aforementioned elements to protect same from damage, for example by dust, water, or excessive impact. According to one implementation of the invention, a printed circuit board 80 is positioned within the housing and has mounted thereon the imaging devices 20a and 20b, processing unit 30, controller 40 and related circuitry arrangements for carrying out the invention. In a preferred embodiment, a sensor such as a 3-axis accelerometer 82 or a gyroscope, is provided to determine the rotation of the imaging devices 20a and 20b with respect to the user. The printed circuit board will also hold a memory device 84, preferably SDRAM, but other types of memory are also contemplated, to store and processes images as they are taken. Various other hardware attached to the printed circuit board or coupled thereto may be necessary to carry out the invention, including additional image processors, PCI, HPI, and EMAC interfaces, power planes and decoupling capacitors. A power supply, internal clocks, an I2C interface, video ports and various relays may be required to run the image processing software as described below. An external memory interface may also optionally be provided.

In one variant of the invention, the imaging device 20 comprises a time of flight camera. The implementation and operation of such a camera are discussed in more detail further below.

The algorithms for use with the device and according to the method of the present invention will now be described. It will be understood by those skilled in the art that these descriptions are by example only and other algorithms which perform equivalent functions may also be used.

The device of the present invention locates objects in three dimensions based on stereoscopic digital images, three axis accelerator (or similar sensor) readings and known geometry. Algorithms that may optionally be run include digital image correction, and stereoscopic image correspondence. The following describes the step by step process from stereo images to three dimensional reconstruction, to activation of vibrating vibro-tactile devices according to the present invention.

Figure 5:
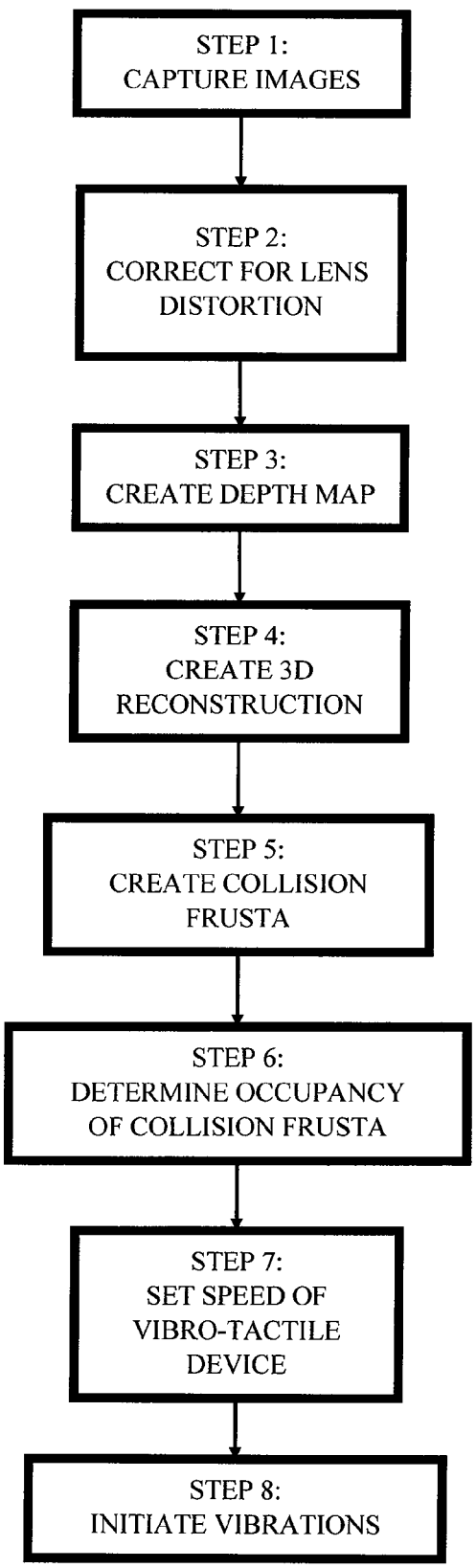
FIG. 5 is a flowchart showing a method in accordance with the invention.
Figure 6A:
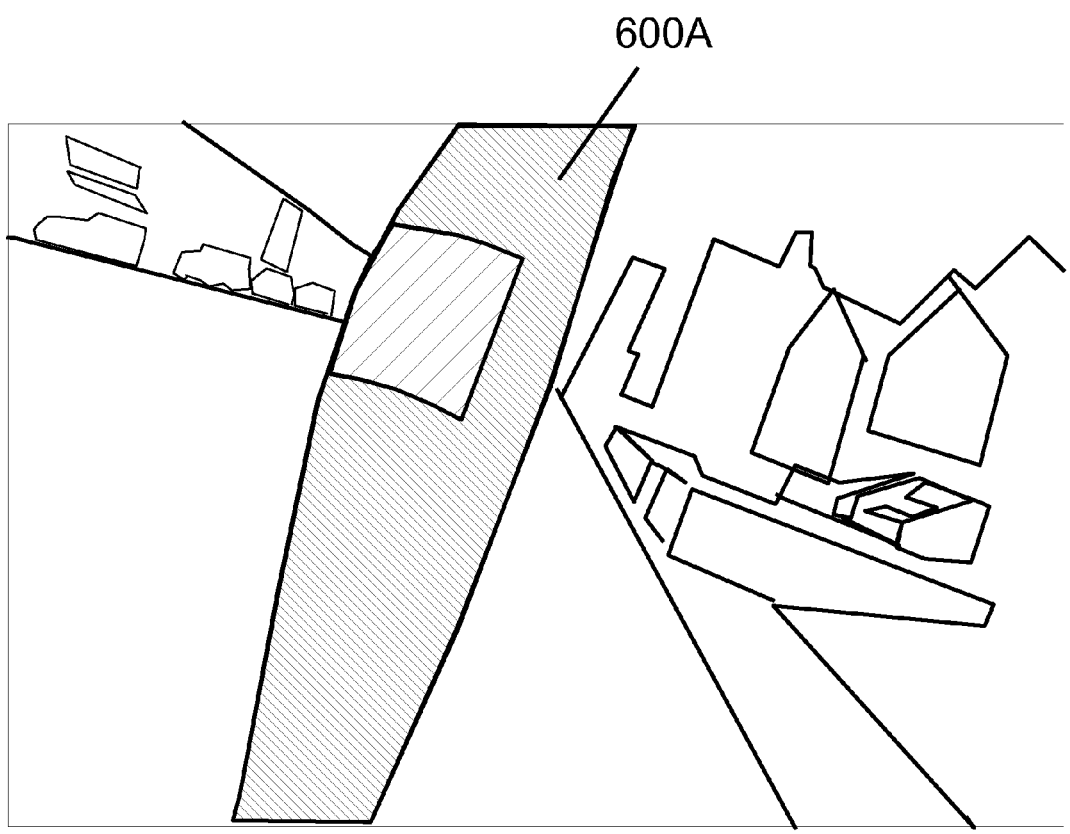
FIGS. 6A-6D are raw and rectified images as used by the invention.
Figure 6B:
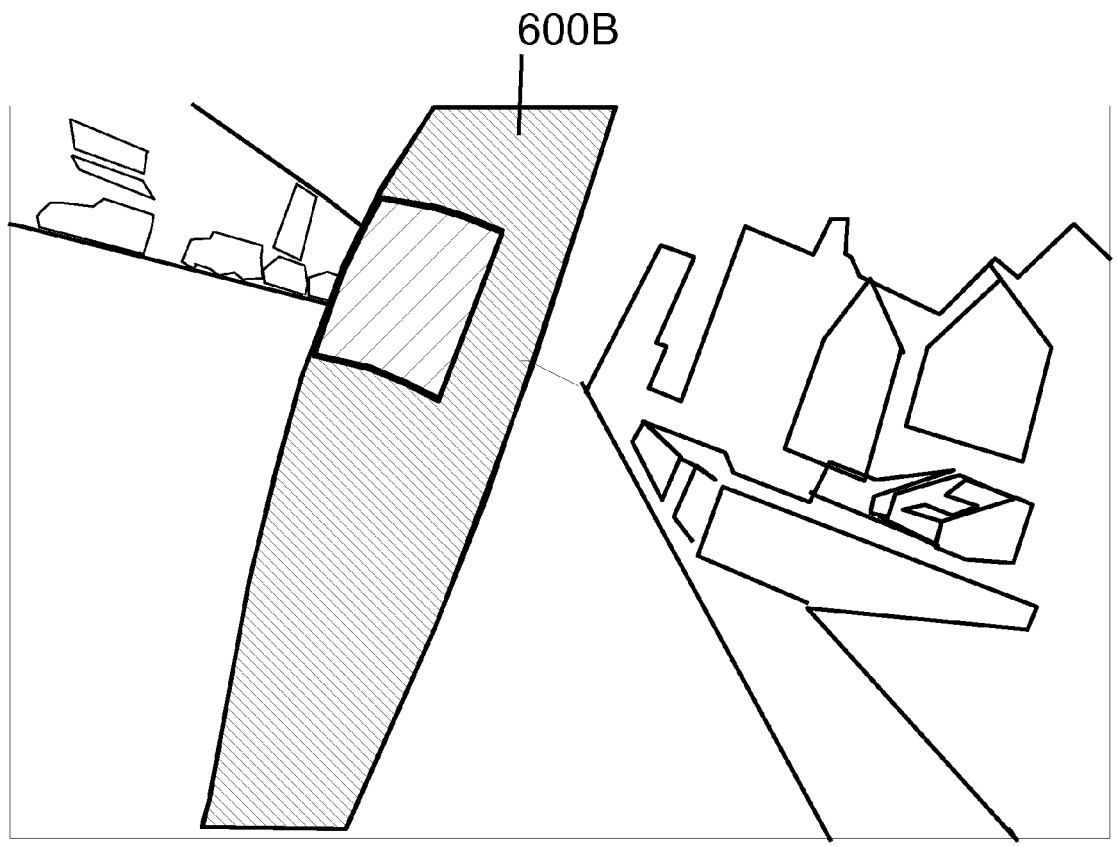

Referring now to FIG. 5, in step 1, the imaging device captures two digital images. The digital images are preferably captured simultaneously from the two, left and right, imagers. The two imagers are preferably spaced apart laterally, for example, at a distance of approximately 5 cm. It will be understood by those skilled in the art that other orientations of the imagers and non-lateral spacing arrangements are equally within the scope of the invention. These captured images are referred to as raw images. FIGS. 6A and 6B show left and right raw images of a street scene, respectively, as would be encountered by a typical user of the device. It will be noted that in both raw images, the lamp post 600A and 600B in the foreground appears curved. This curvature is due to lens distortion. Objects in the left raw image do not match the same horizontal row in the right image. It is therefore necessary to reduce, or eliminate, this curvature and process the images such that an accurate representation of the scene may be obtained.

Figure 6C:
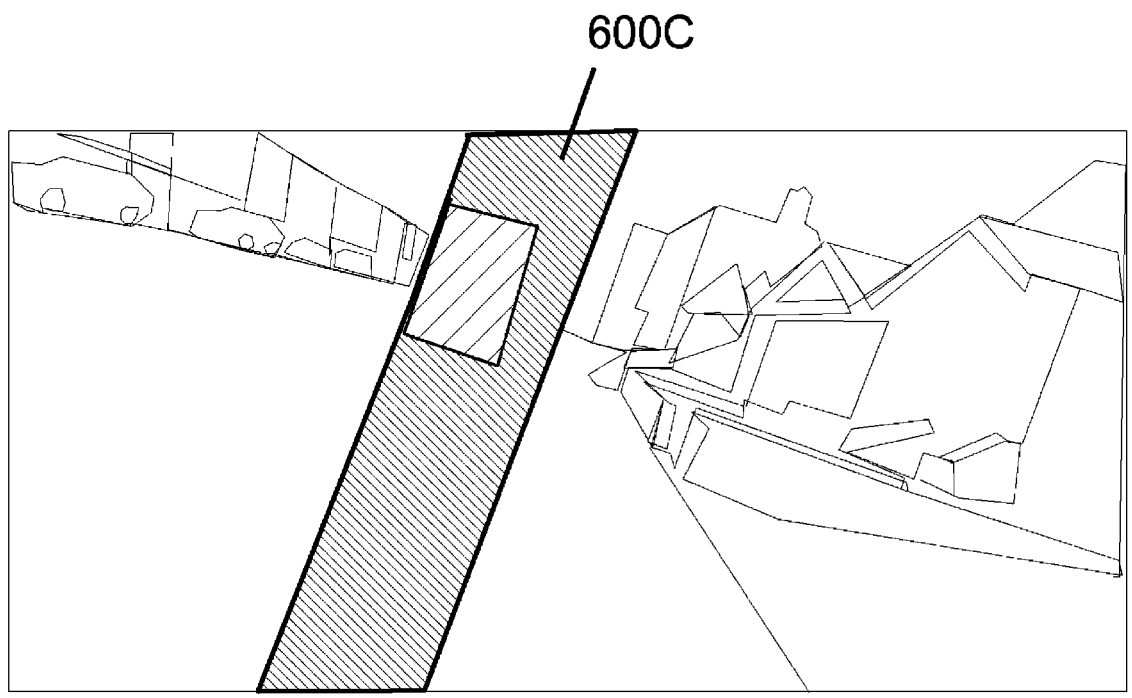
Figure 6D:
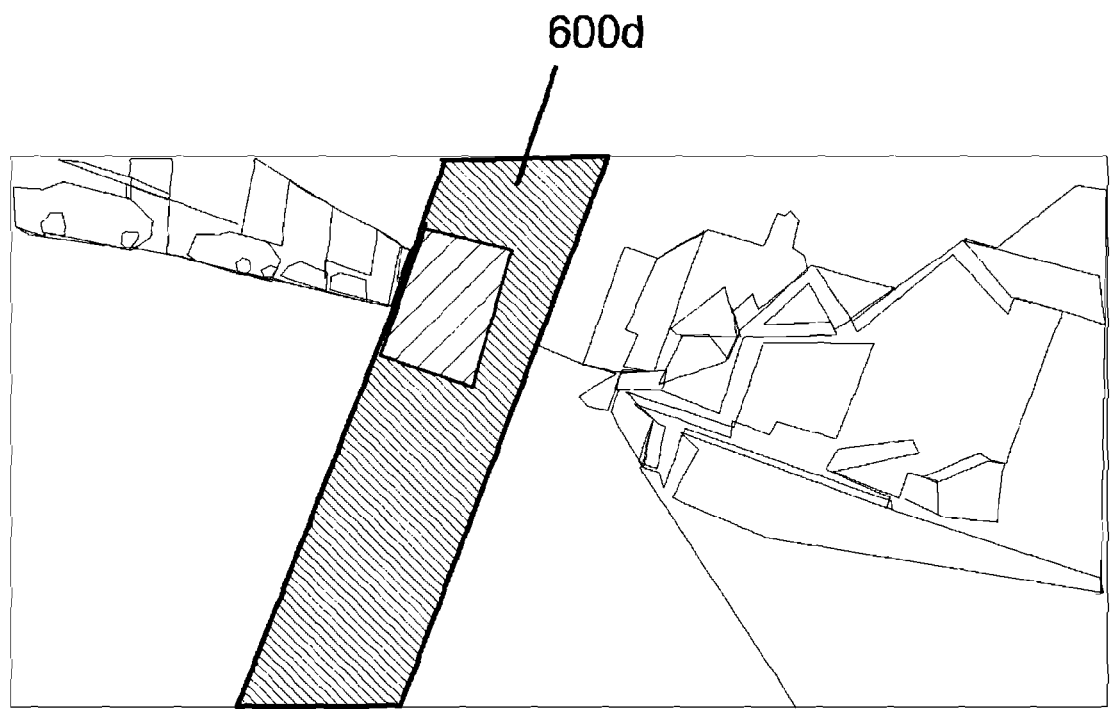

In step 2, the processor, and preferably the image processor corrects the effects of lens distortion and further aligns the pair of images horizontally. After image processing, the new left and right images are herein referred to as the "rectified" images. FIG. 6C is a left rectified image as processed by the device of the present invention. FIG. 6D is a right rectified image as processed by the device of the present invention. Note that in the FIG. 6C and FIG. 6D the lamp post 600C and 600D in the foreground is no longer curved. The lamp post now appears straight. In addition, objects in the left image now align in same horizontal image row as in the right image. Various methods of correcting for lens distortion and aligning stereoscopic images are known in the art and may be used with the invention.

Figure 7A:
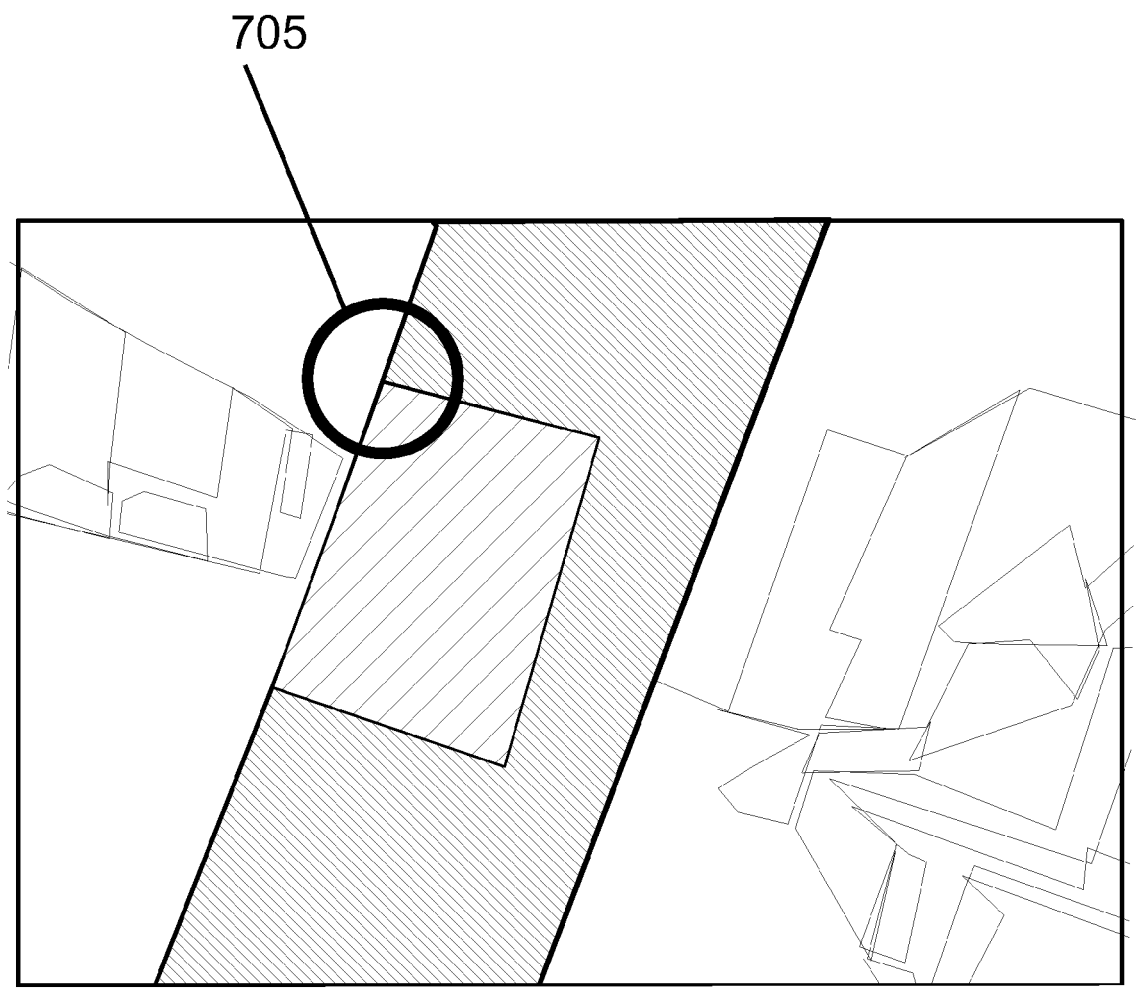
FIGS. 7A and 7B show images being processed in accordance with the invention.
Figure 7B:
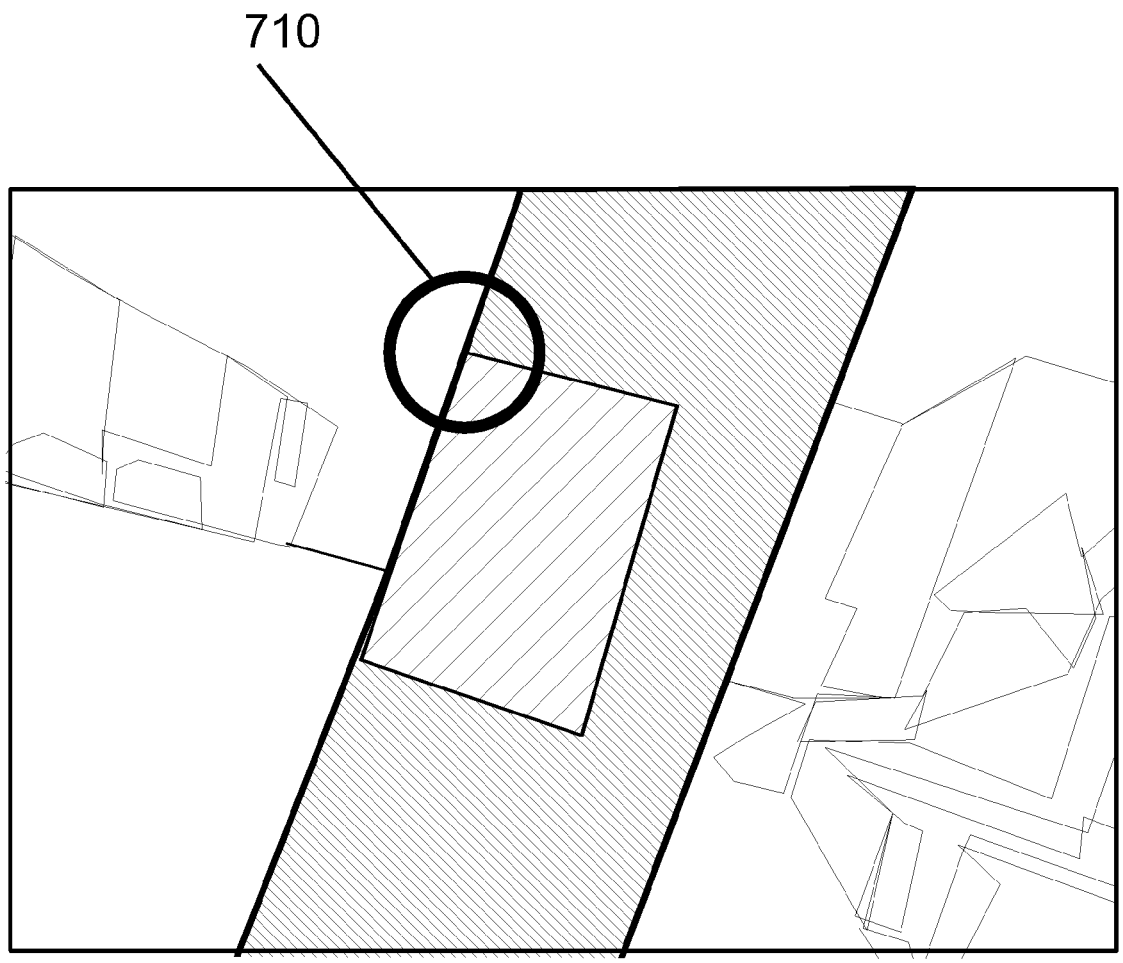

In step 3, with the rectified images now aligned, specific areas in the left and right images are matched up to create a depth map of the scene. FIG. 7A is a close-up of the left rectified image. A circle 705 shows the top left corner of a sign on the pole. FIG. 7B is a close-up of the right rectified image with a matching circle 710 on the top left corner on the pole. The image processor determines that the corresponding locations are offset by some number of pixels, in this case 5 pixels, from each other in the left and right rectified images. This step continues until all objects in the left rectified image are matched to objects in the right rectified image, that is, until an offset of pixels is computed for every pixel in the image.

Figure 8:
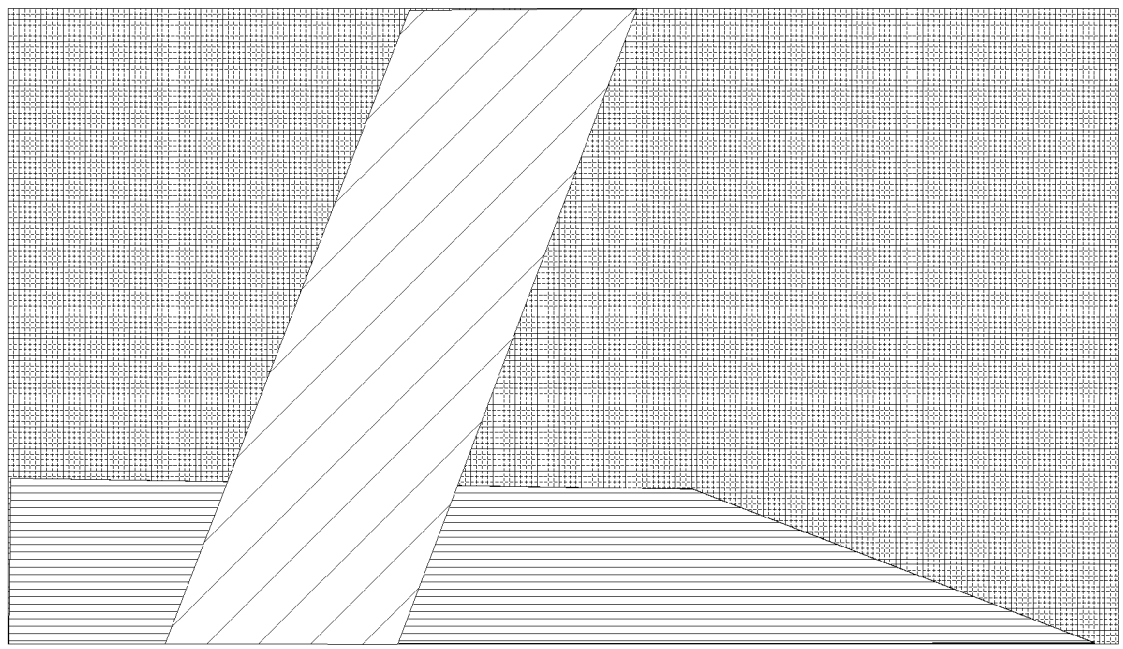
FIG. 8 shows a representative depth map in accordance with the invention.

Then, by matching successive images in both left and right images, a depth map is created. The depth map is an image that has the same dimensions in the plane of the screen as the rectified images, but is representative of the difference in depth between images in each picture. The pixel value in the depth map is a value of the left to right shift of objects in the left image versus the same object in the right rectified image. An exemplary resultant depth map is shown in FIG. 8. While the data held in the depth map includes a depth value for each pixel, as represented on screen, the depth map is gray scaled, for example, light gray represents a disparity of 5 pixels, gray represents a 20 pixel disparity and black a 0 pixel disparity. Each pixel in the depth map holds a pixel value that represents the horizontal disparity of the matching locations in the left rectified image to the right rectified image. For example, if a point in the left rectified image is 5 pixels to the right of the corresponding object in the right rectified image, then the depth map will hold the value "5" for this pixel. Thus, by comparing left and right stereoscopic images, the relative depths of objects can be calculated in accordance with the above description to determine areas in the scene with objects closer and further away from the user.

Figure 9:
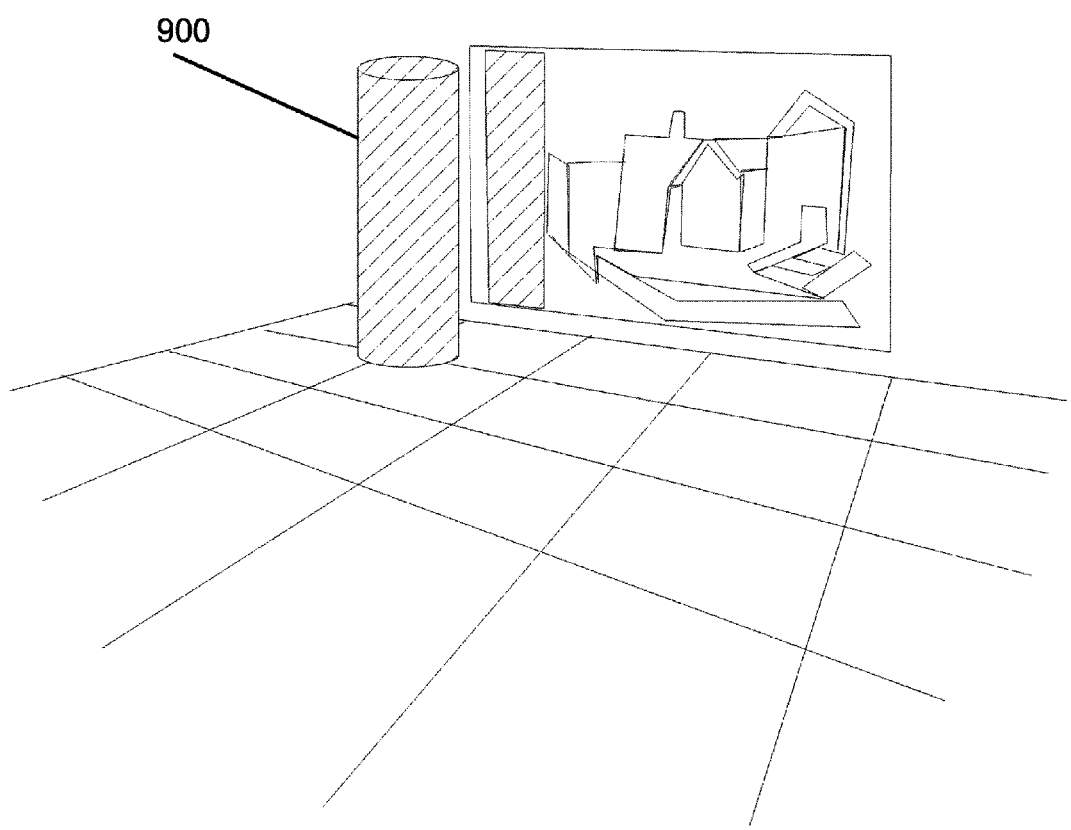
FIG. 9 shows a representative three dimensional space as generated in accordance with the invention; and, FIG. 10 shows a schematic view of the three dimensional space in front of a user divided into volumes of space.

In step 4, a three dimensional reconstruction is created based on measurements from the depth map. Based on individual pixel depth values, each point in the scene as represented by a pixel in the depth map is assigned a depth value, and accordingly is representative of a point in three dimensional space. FIG. 9 is a perspective view of a scene derived from depth map and according to the image processing of the present invention. Position 900 is the lamp post. Note that the original right image used to interpret the street scene is now rotated to be aligned vertically. Rotation is calculated from the data from the 3-axis accelerometer. The three dimensional calculation uses the depth map, the camera intrinsics, and trigonometry. This calculation is based on the field of view of the camera lens. Camera intrisics include camera focal length, image dimensions, and camera focal center. Such calculations will be apparent to those skilled in the art. Every point in the depth map is given a three dimensional position in the three dimensional reconstruction. Each of these three dimensional positions is used in the next step of occupancy mapping.

One of the possible problems associated with the above approach is when the imaging devices are tilted, or become tilted as the user moves around. To accommodate this, a three axis accelerometer may be used to calculate the tilt of the camera. This tilt information is used to rotate the three dimensional scene into the vertical or upright orientation. Alternatively, a gyroscope can be designed into the device for enhanced position sensing. A three axis gyroscope would add more accuracy to the tilt sensing. The result of adding a three axis gyroscope to the three axis accelerometer would result in more precise six axis orientation. The height of the camera above the ground may also be used in the calculations to properly place objects in the three dimensional space.

Figure 10:
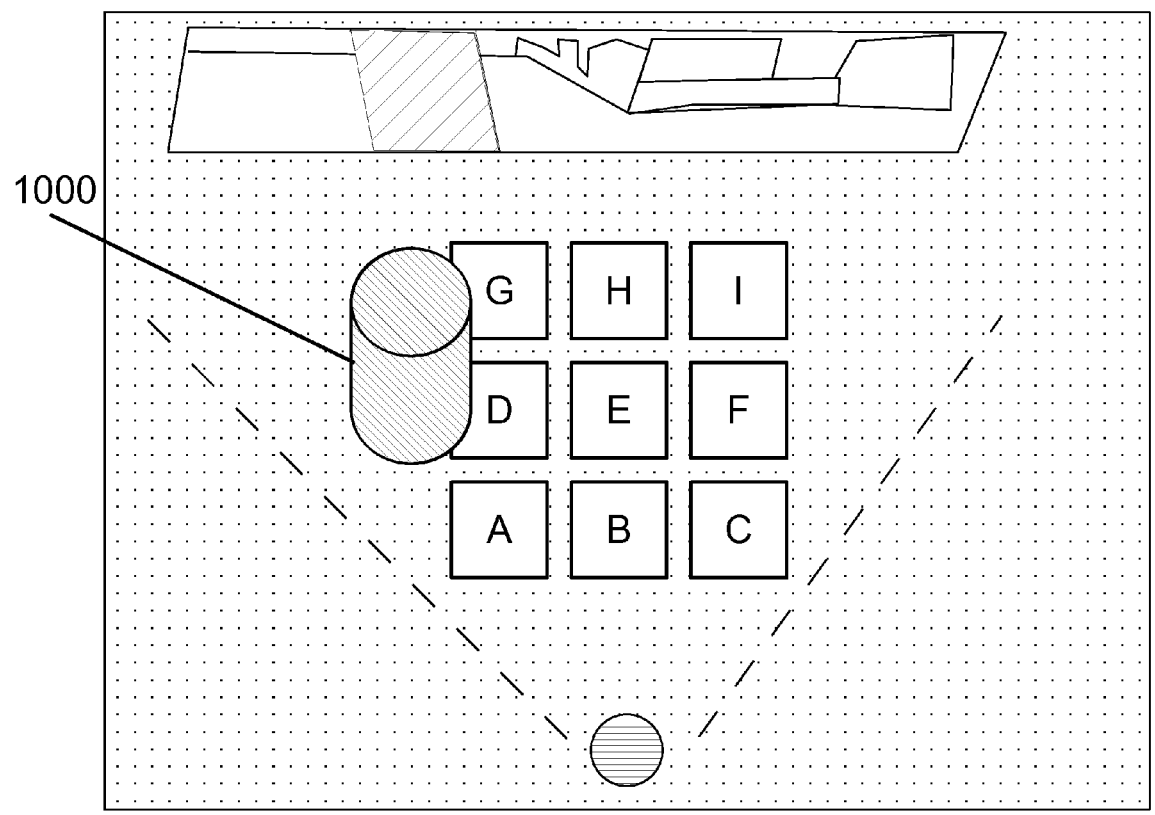

In step 5, the three dimensional space in front of the user is divided into three dimensional volumes, referred to herein as a collision frusta. Each collision frusta has a three dimensional location and orientation relative to the user. The number of three dimensional points in each collision frusta is then counted. In the following example, a collection of nine collision frusta is used to determine the location of above ground objects that are in front of the user. FIG. 10 is a top down view of the three dimensional reconstruction. The outlines of the above ground collision frusta are indicated at 1000. The collision frusta have been projected onto the two dimensional ground planes. The letters A, B, C denote the location of the first row of three collision frusta closest to the camera. Collision frusta "A" is to the left. "B" is center. "C" is to the right. Letters D, E, F denote the middle row of the next three collision frusta. The letters G, H, and I denote the furthest row of three collision frusta. The area 1000 is shown to overlap both collision frusta "D" and "G". The area 1000 in collision frusta "D" and "G" shows the 3D points found from the lamp post. The lamp post thus is found to occupy collision frusta "D" and "G".

Many other collision frusta types can be created and used for detecting specific hazards to the user. For example a collision frusta can be added to determine if the user is about to fall down a stairway or off a railway platform onto a railway track. In this case a collision frusta can be created to detect the presence or absence of the floor before the user. Call this new collision frusta a "floor" collision frusta. If no floor or sidewalk is detected in this "floor" collision frusta, it can be assumed that the user is about to fall. The vibrations can be activated to alert the user of this danger. Another collision frusta can be used for alerting the user of head level obstacles. Collision frusta can be created specifically for the volume of space directly before the user's head. Let us call this the "head" collision frusta. When three dimensional points in the three dimensional reconstruction are found to be in head collision frusta, then the user can be alerted to this danger by activation of the vibrating motors.

In an alternate embodiment, a speaker adapted to emit a beeping sound is included in the system 10. In order to alert the user of head level obstacles, the speaker emits a beep. In this manner, a heightened sense of urgency is provided to head level obstacles and to differentiate from the directional indicators provided by the vibro-tactile interfaces. In this manner, a clear distinction is provided between head level obstacles and other obstacles located in front of the user.

In step 6, the occupancy of collision frusta from three dimensional points is determined. A determination of the occupancy of the collision frusta is done based on the number of three dimensional points found to lie in each collision frusta. To do this a count is made for each collision frusta to keep track of the number of three dimensional points that are within the bounds of the collision frusta. The three dimensional points in the three dimensional reconstruction are compared to the bounds of each collision frusta in turn. If a three dimensional point is found to be within the bounds of a collision frusta, then the count for that collision frusta is incremented. There can be many arbitrarily shaped collision frusta. The three dimensional frusta can be of any shape. A three dimensional point can be found to be within the bounds of more than one frusta. For example, if the number of three dimensional points in Frusta "D" be greater than a minimum number, say 1000, then Frusta "D" will be deemed to be "occupied". The table below shows an example of collision frusta occupancy. The table below shows that collision frusta "D" and "G" are occupied. The table also shows how the example collision frusta A, B, C, are laid out before the person.

| COLLISION FRUSTA | left | center | right |
| --- | --- | --- | --- |
| far row | G-occupied by lamp post | H | I |
| middle row | D-occupied by lamp post | E | F |
| near row | A | B | C |

In step 7, the vibro-tactile device speed control is set based on the collision frusta occupancy. This allows the degree of vibration to be set depending on the distance of the detected objections. Once the collision frusta occupancy has been computed, then this occupancy is mapped to vibro-tactile device speed by a controller. Each of the three vibro-tactile devices, the left, right and center can be turned on or off. Each vibro-tactile device can have its speed controlled by pulse width modulation of the power leads.

In the following example there are nine collision frusta. One example of how to determine to activate a vibrating vibro-tactile device can be done by a one to one match of collision frusta occupancy to speed and location. The table below shows which of the three vibrating interfaces is activated at particular speeds. Motors speed can be off, low, medium, or high speed.

| | left | center | right |
| --- | --- | --- | --- |
| far row | G = left low speed | H = middle low speed | I = right low speed |
| middle row | D = left medium speed | E = middle medium speed | F = right medium speed |
| near row | A = left high speed | B = middle high speed | C = right high speed |

When more than one collision frusta are occupied then a priority decision is preferably made. For example, a near collision frusta has priority over a far collision frusta. Center grid collision frusta have priority over a left or right grid location. There are many possible ways to map collision frusta occupancy to motor control. They can be changed by the manufacturer by changing computer software. Also, future implementations will have user controls to allow the user to perform this function.

In step 8, the user sensors the vibrations of the vibro-tactile devices and responds accordingly.

Upon activation vibrations in the vibro-tactile device in the neck strap are produced. The user is now alerted to an obstacle. In the current example this is a lamp post that is both directly in front and slightly to the left front. As the user walks down the street the vibro-tactile devices are updated continuously. The new settings are based on the new captured images. In one embodiment, the speed of the vibro-tactile device is updated eight times per second.

In one variation of the invention, a time of flight camera is used as the imaging device 20, illustrated in the Figures. A time of flight camera is one in which illuminators, such as light emitting diodes, are used to illuminate the scene in front of the camera, and measuring the time of flight of a light signal between the camera and the object to determine the distance between the camera and the object. On additional benefit of the time of flight camera in its application to the invention is that it is able to function without additional external illumination, and therefore, the implementation of a time of flight camera allows the imaging device of the invention to function equally well without any ambient light. The stereo camera systems discussed above require a minimum amount of ambient light, such as from sunshine or other light sources, in order to function optimally.

Furthermore, time of flight cameras provide distance measurements to significantly higher accuracies compared to the stereo camera system of the previous embodiment, and therefore, the accuracy in the depth chart generated is much improved. Furthermore, the higher accuracy is maintained over the full range of application in a time of flight camera. Stereo cameras, on the other hand, have a tendency to produce higher errors as the camera approaches its maximum operating range. While this may seem insignificant since only objects in close proximity to the user are of concern, the use of a time of flight camera permits a single determination of a given scene to be made, without as many iterations of the image processing steps as herein described. Accordingly, the operational battery life of a device according to the invention using a time of flight camera as the imaging device is likely to be improved.

In operation, a time of flight camera generates the depth image internal to the camera. The depth image is a two-dimensional matrix where each element, or pixel, consists of the distance measurement from the camera to a corresponding element in the scene faced by the camera. Therefore, the calculations of the depth map as described above with respect to the stereo cameras may be generated internally to the camera itself, allow for faster image processing, computation times, and improved power consumption. The response time of the vibro-tactile devices will also be improved, providing more accurate feedback.

The inherent problems associated with image processing techniques, such as the inability to process large surfaces or scenes with uniform colour, or scenes that have repeating identical patters, are also mitigated by using a time of flight camera.

In this embodiment, the imaging device 20 preferably comprises a time of flight camera and time of flight camera illuminator, positioned laterally spaced from each other and arranged to take depth images. The time of flight camera and illuminator are preferably mounted within a housing that holds the processing unit, controller, and all related hardware and power elements, such as a battery, preferably a lithium ion battery, and related hardware required to transmit signals to the vibro-tactile devices. The housing preferably includes a cover to enclose the aforementioned elements to protect same from damage, for example by dust, water, or excessive impact. According to one implementation of the invention, a printed circuit board is positioned within the housing and has mounted thereon the imaging devices, processing unit, controller and related circuitry arrangements for carrying out the invention. In a preferred embodiment, a sensor such as a 3-axis accelerometer or a gyroscope, is provided to determine the rotation of the imaging devices and with respect to the user. The printed circuit board will also hold a memory device, preferably SDRAM, but other types of memory are also contemplated, to store and processes images as they are taken. Various other hardware attached to the printed circuit board or coupled thereto may be necessary to carry out the invention, including additional image processors, PCI, HPI, and EMAC interfaces, power planes and decoupling capacitors. A power supply, internal clocks, an I2C interface, video ports and various relays may be required to run the image processing software as described below. An external memory interface may also optionally be provided.

This concludes the description of a presently preferred embodiment of the invention. The foregoing description has been presented for the purpose of illustration and is not intended to be exhaustive or to limit the invention to the precise form disclosed.

What is claimed is:

1. A system for assisting a visually impaired user comprising:
a time of flight camera;
a processor executing instructions from memory to: receive images from said time of flight camera and convert said images into signals transmitted to one or more controllers;
one or more vibro-tactile devices;
wherein said one or more controllers activates one or more of said vibro-tactile devices in response to said signals received from said processor;
a lanyard means sized and otherwise dimensioned to be worn around a neck of the user, wherein said one or more vibro-tactile devices are mounted on said lanyard means;
a sensor for determining the rotation of the imaging device with respect to a vertical orientation; said rotation being used by said processor to align said images with the vertical orientation prior to generating the signals for use by the one or more controllers;
wherein said signal is transmitted to said one or more controllers; said one or more controllers activating one or more of said vibro-tactile devices in response to said signal; said one or more vibro-tactile devices including a first vibro-tactile device being activated when said signal indicates the presence of an object generally to the right of said user, a second vibro-tactile device being activated when said signal indicates the presence of an object generally to the left of said user; and, a third vibro-tactile device being activated when said signal indicates the presence of an object generally in front of said user.

2. A system according to claim 1, wherein said time of flight camera and said processor are mounted at a bottom end of said lanyard means such that said time of flight camera and said processor are positioned proximate a chest portion of the user when said lanyard means is worn.

3. A system according to claim 1, wherein said time of flight camera is positioned and arranged to provide depth images, or depth maps to said processing unit.

4. A system according to claim 3, wherein said processor includes an image processor.

5. A system according to claim 4, wherein said processor creates a three-dimensional reconstruction based on data from said depth map; and wherein the three-dimensional space in front of the user is divided into a plurality of volumes of space; said processor determining whether objects in front of the user reside in one or more of said plurality of volumes of space; said processor further producing a signal representative of said one or more volumes of space occupied by said objects; wherein said signal is representative of a direction and distance from said user of said objects.

6. A system according to claim 1, wherein said controller activates said vibro-tactile devices with an intensity proportionate to the distance from said user of said objects.

7. A system according to claim 5, further comprising audio alert means; wherein said controller activates said audio alert means when said signal indicates the presence of said object at face level of said user.

\* \* \* \* \*